US011170324B2

(12) United States Patent
Bhavani

(10) Patent No.: US 11,170,324 B2
(45) Date of Patent: Nov. 9, 2021

(54) INTELLIGENT ROUTING OF PATIENTS USING DISTRIBUTED INPUT DEVICES

(75) Inventor: Neeraj Bhavani, Ladera Ranch, CA (US)

(73) Assignee: TAGNOS, INC., Ladera Ranch, CA (US)

( * ) Notice: Subject to any disclaimer, the term of this patent is extended or adjusted under 35 U.S.C. 154(b) by 0 days.

(21) Appl. No.: 12/259,427

(22) Filed: Oct. 28, 2008

(65) Prior Publication Data

US 2009/0051546 A1  Feb. 26, 2009

Related U.S. Application Data

(63) Continuation-in-part of application No. 11/733,056, filed on Apr. 9, 2007, now Pat. No. 9,928,343.

(60) Provisional application No. 60/984,809, filed on Nov. 2, 2007, provisional application No. 60/822,737, filed on Aug. 17, 2006, provisional application No. 60/791,058, filed on Apr. 10, 2006.

(51) Int. Cl.
| | | |
|---|---|---|
| *G06Q 10/06* | (2012.01) | |
| *G16H 40/20* | (2018.01) | |
| *G16H 40/00* | (2018.01) | |

(52) U.S. Cl.
CPC ............ *G06Q 10/06* (2013.01); *G16H 40/00* (2018.01); *G16H 40/20* (2018.01)

(58) Field of Classification Search
CPC ........ G16H 40/20; G16H 10/06; G16H 40/00; G06Q 10/087; G06Q 10/06; G06Q 10/08; G06Q 10/1097; A61B 5/1113; A61B 5/1112; G01V 15/00; F25D 2700/08; H04W 64/00; H04W 4/02; H04W 4/029
USPC ........................................................ 705/2–3
See application file for complete search history.

(56) References Cited

U.S. PATENT DOCUMENTS

| | | | | |
|---|---|---|---|---|
| 5,748,907 A | * | 5/1998 | Crane | .................... G06Q 10/06 705/2 |
| 6,466,125 B1 | | 10/2002 | Richards et al. | |
| 6,970,097 B2 | * | 11/2005 | Welles, II | ............... G01S 1/725 340/539.13 |
| 7,382,247 B2 | | 6/2008 | Welch et al. | |
| 7,480,629 B2 | | 1/2009 | Dashefsky et al. | |
| 2002/0029272 A1 | * | 3/2002 | Weller | .................... G06Q 10/06 709/226 |
| 2003/0061090 A1 | * | 3/2003 | Marano | .............. G06Q 10/1097 705/7.21 |
| 2004/0100380 A1 | * | 5/2004 | Lindsay | ............. G06K 19/0717 340/540 |
| 2004/0204963 A1 | | 10/2004 | Klueh et al. | |
| 2005/0092825 A1 | | 5/2005 | Cox et al. | |
| 2005/0102167 A1 | * | 5/2005 | Kapoor | .................. G16H 20/17 705/3 |
| 2005/0149358 A1 | | 7/2005 | Sacco et al. | |
| 2005/0216212 A1 | | 9/2005 | Bellin et al. | |
| 2005/0258937 A1 | * | 11/2005 | Neuwirth | .................. H04B 1/04 340/5.92 |
| 2006/0151424 A1 | | 8/2006 | Graves et al. | |
| 2006/0178913 A1 | | 8/2006 | Lara et al. | |
| 2006/0192655 A1 | * | 8/2006 | Levin | .................... G06K 7/0008 340/10.2 |
| 2006/0282302 A1 | | 12/2006 | Hussain | |
| 2007/0129983 A1 | | 6/2007 | Scherpbier et al. | |
| 2007/0139191 A1 | * | 6/2007 | Quatro | .................... G06Q 10/08 340/539.13 |
| 2007/0288263 A1 | * | 12/2007 | Rodgers | .................. G16H 40/20 705/2 |

FOREIGN PATENT DOCUMENTS

| | | | | |
|---|---|---|---|---|
| WO | WO 2005/045461 A1 | * | 5/2005 | ............... G01S 5/02 |
| WO | WO 2005045461 A1 | * | 5/2005 | ............... G01S 5/02 |
| WO | WO-2005045461 A1 | * | 5/2005 | ........... G01S 5/0226 |

OTHER PUBLICATIONS

John W. Basch, Available System and Technologies, Oct. 1, 2000, http://www.infectioncontroltoday.com/view/available-systems-and-technologies (Year: 2000).*
Basch, Available System and Technologies, Oct. 1, 2000, http://www.infectioncontroltoday.com/view/available-systems-and-technologies (Year: 2000).*
http://informationweek.com/story/ showArticle.jhtml?articleID=162101504). The Cisco™ article.

* cited by examiner

*Primary Examiner* — Joy Chng
(74) *Attorney, Agent, or Firm* — Fish IP Law, LLP

(57) ABSTRACT

A system and method for intelligently routing patients on-the-fly inside a hospital is contemplated. Patients and resources are tagged to allow a central clearing house to track their location. Using the location information, the central clearing house can then dispatch commands to bring patients to resources, or vice versa. The tags can be any type of real-time location system, including ultrasound or radio frequency identification tags.

17 Claims, No Drawings

INTELLIGENT ROUTING OF PATIENTS USING DISTRIBUTED INPUT DEVICES

This application is a continuation-in-part of non-provisional application Ser. No. 11/733,056 filed Apr. 9, 2007. Ser. No. 11/733,056 claims priority to (1) provisional application No. 60/791,058 filed Apr. 10, 2006, and (2) provisional application No. 60/822,737 filed Aug. 17, 2006. This application also claims priority to provisional application No. 60/984,809 filed Nov. 2, 2007. All prior applications are incorporated by reference in their entirety.

FIELD OF THE INVENTION

The field of the invention is hospital asset management systems.

BACKGROUND

Healthcare enterprises, whether hospitals, nursing homes, surgical centers, physician's offices and so forth, all have challenges tracking their various assets. One problem is that such facilities typically contain a large number of different types of assets, including for example, rooms, gurneys, diagnostic equipment, treatment equipment, bandages and other supplies, drugs, and so forth. Another problem is that such assets are often mobile, and during the course of even a single day can be present at different times in a dozen or more different locations. Similar problems exist for personnel assets, including for example, physicians, nurses, technicians, and other personal.

In addition to difficulties in tracking assets, healthcare enterprises encounter significant difficulties in efficient utilization of assets. That situation occurs for numerous reasons, including for example the fact that many assets are only usable upon cleaning or other preparation, and many are suitable only in combination with other assets. Thus, an x-ray machine might only usable when there is a qualified x-ray technician available to operate it, and a physician might only be able to perform a surgical procedure when accompanied by a nurse having an appropriate skill set.

Healthcare enterprises have made considerable strides over the years in implementing computer systems that address materials management, bed management, staff timekeeping, pharmacy and lab procedures and reporting, and billing. Many enterprises have also implemented applications for specific departments, including for example the emergency rooms (ER), operating rooms (OR), intensive care unit (ICU), and cardiac care units (CCU). Unfortunately, many of these systems have trouble communicating with each other, and some do not communicate with other systems at all. Such lack of communication can significantly reduce efficiency and increase costs.

One might image that manufacturers of the existing systems would develop enterprise wide solution, and indeed in some instances that process is going forward. But enterprise-wide solutions run into enormous problems, not least because manufacturers commonly try to implement proprietary systems and methods that exclude their competitors, and that approach triggers enormous resistance from physicians and staff that might be force to adopt technologies with which they are unfamiliar or comfortable.

It is known that Radio Frequency Identification Tags (RFID tags) can be used to keep tabs on the locations of equipment, supplies, and so forth, and there are already systems on the market that utilize such information for specific applications. For example, there are RFID tag systems that are suitable for keeping track of locations of assets. In 2005 CISCO™ announced its WIRELESS LOCATION APPLIANCE™ 2700 device, which uses WiFi access points to gather signal strength indicators from 802.11 devices and tag, and triangulates the information to roughly determine the locations of the devices.

It is also known that RFID tags can be used to obtain and transmit physical parameters data (e.g., time, temp, and moisture, etc), and operational data (e.g., on/off, ready/not ready, damaged, being cleaned, etc). Several manufacturers have already announced plans to include such tags in their equipment, but there do not appear to be any such systems in common use.

Our previous application with Ser. No. 11/381,060 taught a VoIP communicator using an ultrawide band frequency that could be used as such a tag. Our previous application with Ser. No. 11/733,056 taught how Radio Frequency Identification Tags (RFID tags) can be used with multiple different computer systems in a healthcare environment. Unfortunately, with current technology, RFID tags can be costly, and RFID signals can encounter interference from nearby metal objects. Thus, there is still a need in the art for more cost-effective and more robust tagging systems.

Additionally, where hospitals already use tagging systems, another issue arises from the ease with which tags can be readily duplicated. For example, some nurses duplicate the bar code and keep the duplicates at the nursing station. The nurses then scan the bar codes and the medical treatments at the nursing station to save time, and consequently deliver the medical treatments to patients without the appropriate scanner verification.

Thus, there is still a need for a robust system that helps to reduce the probability of a hospital worker administering the wrong treatment to a patient.

SUMMARY OF THE INVENTION

The present invention provides apparatus, systems, and methods in which an RFID, ultrasound, or other tags is used for real time re-routing of patients or resources in a hospital or other medical setting.

Patients, resources, and sometimes hospital workers are tagged with tags, which can be tracked using a real-time location system. Preferably, the location system tracks the locations of the tags in three dimensions and reports any change in location in real-time to a central database system. By keeping track of the tags, the system keeps track of the locations of patients, resources, and sometimes even hospital workers in the medical facility. Preferably, the hospital workers have communicators with tags allow the hospital worker to convey more than just location information to the central database system.

Since the computer system keeps track of patients, resources, and workers, if a patient requires a resource, the system could find the nearest worker and instruct that worker to move the patient to the resource, or the resource to the patient. The system could use any suitable rule-based logic to initiate the instruction. For example, the movement of a patient falling to a floor could trigger a worker to bring a doctor to the patient, or a scheduled time to take medicine could trigger a worker to bring medication to the patient.

DETAILED DESCRIPTION OF THE INVENTION

In preferred embodiments patients and resources are tagged with communicators to allow a "central clearing house", (e.g., a central database or computer system), to track their status. Using this information, the central clearing house can assign or reassign tasks to increase efficiency based upon a change of a status, for example a patient changing location or a resource becoming available. The communicators are preferably cost-effective, yet difficult to duplicate.

A communicator can advantageously comprise a circuit, a microphone, and a speaker that cooperate to perform VoIP, and an active responder that utilizes an ultrasound frequency. While an ultrasound frequency is preferred, the active responder could use any real-time location system (RTLS), such as radio frequency identification. The term VoIP is to be interpreted here in its broadest sense, to include use of any suitable technology, including for example IP, ARP, UDP, TCP, ICMP, Telnet, TFTP, AutoIP, DHCP, HTTP, and SNMP. It is especially contemplated that communication can comply with any of the 802.11x or superseding standards.

The communicator can be quite simple, or more elaborate, such as for example including a display screen. The display preferably uses color images, and more preferably displays output of a rich colored asset mapper. Contemplated communicators can optionally include cell phone circuitry, walkie-talkie circuitry, and other features such as a biometric scanner.

In other aspects of the inventive subject matter, a system utilizing the inventive communicators can include a processor that cooperates with the responder to determine a location of the responder to within 1 meter, and more preferably to within 0.5 meters, 0.1 meters, or less. This accuracy can be accomplished in any suitable manner, including especially use of an ultrawide band frequency or an ultrasound frequency.

Contemplated methods include identifying a location of an asset to a user through voice commands. For example, it is contemplated that a user could say make a sound, such as a word or a number, into a communicator to identify the asset. A computer system could then use the identifier to select an available asset from among a plurality of assets within a class, could automatically determine the location of the available asset to within 10 meters; and could cause the communicator to display information regarding the location of the asset. Such methods are especially contemplated for mobile assets such as people, equipment, and supplies. This is especially important for hospitals and other large medical practices where cell phones are often jammed and alternative methods of communication are necessary. In a particularly useful embodiment, a user can speak the name of a class of objects into the communicator (e.g. I need a gurney"), and the system can determine which of the plurality of assets of the class (e.g. gurneys) is physically nearest to the user. The location of the asset can be determined in any suitable manner, including triangulating a signal from a voice communicator carried by the user. Preferably the location of the asset can be determined in three dimensions, since many hospitals have multiple floors, and some assets may be hidden behind other assets. All suitable methods of triangulation are contemplated, including triangulating differential times of reception of a given signal, triangulating phase differences in reception of a given signal, and/or triangulating differential signal strengths in reception of a signal.

In yet another aspect of the inventive subject matter, a system could comprise a plurality of portable communicators, each of which includes a circuit, a microphone, and a speaker that all cooperate to allow voice communication using a transmission protocol, such as VoIP, across the system, a plurality of assets tagged with an active responder, and a processor that cooperates with the communicators and the responders to determine the locations of the assets and the communicators to within 1 meter. The system can be implemented locally or distally to a hospital or other business. In the latter instance the system can be operated as an application service provider (ASP) or a product-as-service. Several novel software functionalities are contemplated, including: (a) reporting the location of the responder as being within one of a plurality of business locations; (b) using scalar vector graphics to display the locations with varying degrees of detail; (c) displaying replay of movements of the assets; (d) displaying utilization profiles of the assets; and (e) coordinating the locations of the at least some of the assets data from a global satellite positioning system (GPS). It is still further contemplated that different ones of the responders can operate with first and second different middleware, different frequencies, different types of interrogators, etc, and that the inventive system can nevertheless consolidates output from the different types of equipment. This could be viewed as an "air-traffic controller" type of system, in that it can operate with and coordinate with a large number of different systems, some of which can be incompatible with each other.

The location of the responder can be reported in one, two, or even three dimensions. Using a third dimension to report the height of the responder is especially advantageous in medical situations, as a patient may fall or may be located on a different floor than anticipated. It is preferred to detect the location of a responder using RFID or ultrasound technology, although any other suitable technology can be used. In an exemplary embodiment, the location of the responder can be sent to an alert station if the responder moves to an unauthorized location, for example if a patient moves to a different ward or a patient falls to the floor.

In still other aspects, it is contemplated that at least one of the responders in a system cooperates with at least one communicator to effect voice-to-write status and voice-to-read status. For example, responders can advantageously contain memory that can store information communicated orally from a user through the communicator, and responders can contain memory that stores status information regarding one of the plurality of assets. In the latter instance, for example, a user could speak into a communicator "check status of IV pump." In this situation, the query could then be interpreted by the system, the appropriate responder associated with the IV pump could be interrogated with an interrogator for the status, and the resulting information could be sent back to the communicator for display or auditory presentation.

Various objects, features, aspects and advantages of the present invention will become more apparent from the following detailed description of preferred embodiments of the invention, along with the accompanying drawings in which like numerals represent like components.

The present invention also provides apparatus, systems, and methods in which ultrasound information is provided for multiple different purposes in a scalable, flexible manner, preferably using rules and correlations that can be altered by healthcare staff having little or no specialized information technology (IT) expertise. Such information can be further combined with patient telemetry to provide positional information of the patient and/or associated healthcare personnel.

The ultrasound information will typically include one or more pieces of information regarding the responder's location, physical parameter data, and operational data. It is further contemplated that different types of items can be tagged, including equipment, people, and supplies. Any suitable type of tag, or combinations of different types of tags, can be utilized, with readers (also known as interrogators or transceivers) placed around the enterprise as appropriate. Contemplated systems can have anywhere from a single tag to 5,000 or even more tags in a large enterprise. The readers could advantageously be positioned such that at least 80% of the ultrasound information is refreshed at least every 10 minutes, and but more preferably the system would be implemented so that at least 80% of the ultrasound information is refreshed at least every minute.

The core of the system is contemplated to be embodied in a general purpose computer. Data entry and display devices communicatively coupled to the computer could be positioned throughout the enterprise, and could include electronic tablets, cell phones and pagers, as well as full sized data entry screens and displays such as might be found in accounting departments and nurses stations. In most or even all cases the data entry and display devices need not be dedicated to handling information derived from the ultrasound data. Preferred systems and methods include a Java or other cache that stores current ultrasound information, a rules based engine that derives events from the ultrasound information, a correlation engine that derives steps from the events, and an execution engine that delivers information relating to the steps. Ideally, staff members of the enterprise can define at least one of the rules and correlations entirely using menus and/or point and click techniques.

Events can fall within any appropriate range of generality to specialization. For example, an event might comprise "a doctor reported to the emergency room for duty" or "Dr. Jones reported to the emergency room for duty." The same is true of steps. One step might be to "discharge the patient" and another might be to "send an SMS message to Dr. Jones advising of delay in surgery." All realistic steps are contemplated, including one or more of sending a text message, a page or a voice message, and providing information to disparate systems, including a billing system, a bed management system, a staff timekeeping system, and a medical information system.

In preferred embodiments, a central clearing house communicates simplified messages to a holder of an ultrasound communication device. For example, if a step comprises "discharge the patient," the clearing house could scan the received data to find the closest available nurse and send the message, "Nurse A, please report to room B and discharge patient C." Alternatively, the communication device could have this algorithm built into the firmware so that the human intervention of scanning the received data is not necessary. Or the communication device could issue a warning if a message is inappropriate, for example if a patient is not located in his assigned room. Still further, the communication device could be used to intelligently route patients on-the-fly, for example, by routing a nurse to X-ray room Z when X-ray room Y is suddenly occupied for an emergency.

If a message is sent to the holder of a communication device, for example a nurse, then either the nurse or the communication device could acknowledge receipt of the instruction, preferably through the communication device itself. The same instruction can also be given to multiple communication devices, and can be rescinded once the holder of one of the communication devices accepts responsibility for performing the task. Other combinations are contemplated, for example rescinding an instruction only after a certain number of workers respond, or changing the nature of an instruction based upon a response from either the nurse or the communication device.

The inventive subject matter further provides systems, methods and devices in which are ultrasound circuitry is combined with a telemetry unit. The ultrasound circuitry can be combined with the telemetry unit in any suitable manner, including for example including the circuitry in a tag, and attaching the tag to the telemetry unit, or to a patient wearing the telemetry unit. The ultrasound circuitry preferably uses Ultra-Wide band frequency capability, or other high resolution technology. In especially preferred embodiments the ultrasound circuitry can provide resolution to below five feet in at least some area of a medical care facility that uses the telemetry unit.

In other contemplated uses, the ultrasound circuitry can be used to provide information used in billing use of the telemetry unit, or for some other aspect of billing. Additionally or alternatively, the ultrasound circuitry can provide information that is used to predict an event related to a patient carrying the telemetry unit and/or as input to an information technology software package in a medical care facility.

Currently, the most preferred tags for the inventive subject matter are passive ultrasound tags. Such are relatively more difficult to reproduce than bar codes, and nurses cannot copy a passive tag and bring it to the nursing station. Among other things, this helps ensure that the nurse physically goes to the correct patient when administering medication.

A combination of passive tags and active tags is also contemplated. For example, a given patient can wear an active tag, and a drug or other object could carry a passive tag. When a clinician approaches a patient, the active tag could automatically identify that the appropriate clinician is treating the appropriate patient. The passive tag could then be scanned before the clinician administers the medical treatment, verifies a specimen, etc. The scanning could be carried out in any suitable manner, including for example, using a hand-held scanner. In a preferred embodiment, a single handheld reader would read both passive tags and bar-codes so as to be compatible with both systems. All of this is contemplated to help verify that appropriate medical procedures are used.

Thus, specific embodiments and applications of providing ultrasound information for multiple different purposes in a scalable, flexible manner have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system for tracking a piece of equipment within a medical facility, the system comprising:
   a tag comprising an ultrasound responder and having a memory configured to store an operational status information about the piece of equipment;
   a computer system configured to track a real-time location of the piece of equipment based on ultrasound communication with the tag;
   wherein the computer system is configured to automatically assign a patient routing task to a medical facility worker based on (a) the real-time location of the tag, (b) the operational status information stored in the memory, and (c) the patient requiring the piece of equipment;
   wherein the patient routing task routes the piece of equipment to the patient; and
   wherein the computer system is further configured to re-route the piece of equipment based on at least one of (a) a change in availability of the equipment, (b) a change in location of the patient, or (c) an input by the medical facility worker after the patient routing task is assigned.

2. The system of claim 1, further comprising a communicator having a circuit, a microphone and a speaker, and wherein the computer system is additionally configured to track locations of the communicator, and to assign the tasks to the medical facility workers based in part on the tracked locations of the communicator.

3. The system of claim 1, further comprising a communicator having a circuit, a microphone and a speaker, and wherein the communicator and computer system are collectively configured to process voice queries from medical facility workers, including voice queries for the operational status of the object.

4. The system of claim 1, further comprising a communicator having a circuit, a microphone and a speaker, and wherein the communicator is configured to use voice to write to store the operational status information in the memory.

5. The system of claim 1, wherein the operational status information includes physical parameters data.

6. The system of claim 5, wherein the physical parameters data is selected from the group consisting of temperature and moisture.

7. The system of claim 1, wherein the operational status information includes operational data.

8. The system of claim 7, wherein the operational data indicates the piece of equipment is damaged.

9. The system of claim 1, wherein the computer system is configured to interpret a spoken query from the communicator, and interrogate the tag regarding status of the piece of equipment.

10. The system of claim 1, wherein the tag reports real-time movement of the piece of equipment, wherein the real-time movement is determined by triangulation to less than 1 meter.

11. The system of claim 1, wherein the system interrogates location of the piece of equipment in real-time.

12. The system of claim 1, wherein the real-time location of the piece of equipment is determined by triangulation to less than 1 meter.

13. The system of claim 1, wherein the computer system is further configured to confirm physical proximity of the piece of equipment to the patient.

14. The system of claim 1, wherein re-routing the piece of equipment is based on the change in availability of the equipment.

15. The system of claim 1, wherein re-routing the piece of equipment is based on the change in location of the patient.

16. The system of claim 1, wherein re-routing the piece of equipment is based on the input by the medical facility worker after the patient routing task is assigned.

17. The system of claim 1, wherein the ultrasound responder provides information used to predict an event related to the patient.

* * * * *